US00PP19865P2

(12) United States Plant Patent
Pierce

(10) Patent No.: US PP19,865 P2
(45) Date of Patent: Mar. 31, 2009

(54) *CALIBRACHOA* PLANT NAMED 'CAL PEACHY'

(50) Latin Name: ***Calibrachoa* sp.**
Varietal Denomination: Cal Peachy

(75) Inventor: Robert Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/080,152

(22) Filed: Mar. 31, 2008

(51) Int. Cl.
*A01H 5/00* (2006.01)

(52) U.S. Cl. ..... Plt./413
(58) Field of Classification Search ..... Plt./413
See application file for complete search history.

*Primary Examiner*—Annette H Para
(74) *Attorney, Agent, or Firm*—C. A. Whealy

(57) ABSTRACT

A new and distinct cultivar of *Calibrachoa* plant named 'Cal Peachy', characterized by its mounding and outwardly spreading to trailing plant habit; freely branching habit; dense and full plants; early and freely flowering habit; numerous peach-colored flowers; and good garden performance.

1 Drawing Sheet

Botanical designation: *Calibrachoa* sp.
Cultivar denomination: 'CAL PEACHY'.

BACKGROUND OF THE INVENTION

The present invention relates to a new and distinct cultivar of *Calibrachoa*, botanically known as *Calibrachoa* sp. and hereinafter referred to by the name 'Cal Peachy'.

The new *Calibrachoa* is a product of a planned breeding program conducted by the Inventor in Gilroy, Calif. The objective of the breeding program is to create new *Calibrachoa* cultivars with uniform plant habit and numerous attractive flowers.

The new *Calibrachoa* originated from a cross-pollination made by the Inventor in August, 2004 in Gilroy, Calif. of the *Calibrachoa* sp. cultivar Cal Goldey, disclosed in U.S. Plant Pat. No. 17,303, as the female, or seed, parent with a proprietary selection of *Calibrachoa* sp. identified as code number 1295, not patented, as the male, or pollen, parent. The new *Calibrachoa* was discovered and selected by the Inventor as a single flowering plant within the progeny of the stated cross-pollination in a controlled environment in Gilroy, Calif. in April, 2005.

Asexual reproduction of the new *Calibrachoa* by vegetative cuttings in a controlled environment in Gilroy, Calif. since April, 2005 has shown that the unique features of this new *Calibrachoa* are stable and reproduced true to type in successive generations.

SUMMARY OF THE INVENTION

The cultivar Cal Peachy has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Cal Peachy'. These characteristics in combination distinguish 'Cal Peachy' as a new and distinct cultivar of *Calibrachoa* :

1. Mounding and outwardly spreading to trailing plant habit.
2. Freely branching habit; dense and full plants.
3. Early and freely flowering habit.
4. Numerous peach-colored flowers.
5. Good garden performance.

The new *Calibrachoa* can be compared to plants of the female parent, the cultivar Cal Goldey. Plants of the new *Calibrachoa* differ from plants of the cultivar Cal Goldey in the following characteristics:

1. Plants of the new *Calibrachoa* have smaller and darker green-colored leaves than plants of the cultivar Cal Goldey.
2. Plants of the new *Calibrachoa* and the cultivar Cal Goldey differ in flower color as plants of the cultivar Cal Goldey have gold-colored flowers.

Plants of the new *Calibrachoa* can be compared to plants of the male parent selection. Plants of the new *Calibrachoa* differ from plants of the male parent selection in the following characteristics:

1. Plants of the new *Calibrachoa* have a more prostrate plant habit than plants of the male parent selection.
2. Plants of the new *Calibrachoa* have darker green-colored leaves than plants of the male parent selection.
3. Plants of the new *Calibrachoa* flower earlier than plants of the male parent selection.

Plants of the new *Calibrachoa* can be compared to plants of the cultivar KLEC02004, not patented. In side-by-side comparisons conducted in Hillscheid, Germany, plants of the new *Calibrachoa* differed from plants of the cultivar KLEC02004 in the following characteristics:

1. Plants of the new *Calibrachoa* were more freely branching than plants of the cultivar KLEC02004.
2. Plants of the new *Calibrachoa* flowered earlier than plants of the cultivar KLEC02004.
3. Plants of the new *Calibrachoa* and the cultivar KLEC02004 differed in flower color as flowers of plants of the cultivar KLEC02004 did not have distinct red-colored centers.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph comprises a close-up view of a typical flowering plant of 'Cal Peachy'.

DETAILED BOTANICAL DESCRIPTION

The aforementioned photograph and following observations, measurements and values describe plants grown in Hillscheid, Germany under commercial practice during the summer in an outdoor nursery. Plants used for the photograph were grown in 15-cm containers for about 16 weeks. Plants used for the description were grown in 25-cm hanging basket containers for about seven months. In the following description, color references are made to The Royal Horticultural Society Colour Chart, 2001 Edition, except where general terms of ordinary dictionary significance are used.

Botanical classification: *Calibrachoa* sp. cultivar Cal Peachy.

Parentage:

*Female, or seed, parent.*—*Calibrachoa* sp. cultivar Cal Goldey, disclosed in U.S. Plant Pat. No. 17,303.

*Male, or pollen, parent.*—Proprietary selection of *Calibrachoa* sp. identified as code number 1295, not patented.

Propagation:

*Type.*—By vegetative cuttings.

*Time to initiate and develop roots.*—About 18 to 23 days.

*Root description.*—Fibrous; color, close to 155D.

Plant description:

*Plant and growth habit.*—Mounding and outwardly spreading to trailing plant habit. Freely branching habit with about 20 primary lateral branches each with about five to six secondary lateral branches; full and dense plants. Vigorous growth habit.

*Plant height.*—About 10 cm.

*Plant diameter.*—About 43 cm to 46 cm.

Lateral branch description:

*Length.*—About 25 cm.

*Diameter.*—About 2 mm to 3 mm.

*Internode length.*—About 1 cm to 1.8 cm.

*Strength.*—Strong; flexible.

*Aspect.*—Initially upright to outwardly spreading to trailing.

*Texture.*—Densely hirsute.

*Color.*—Close to 143C.

Foliage description:

*Arrangement.*—Alternate, simple.

*Length.*—About 3.1 cm to 3.5 cm.

*Width.*—About 1.2 cm to 1.4 cm.

*Shape.*—Elliptic to lanceolate.

*Apex.*—Rounded.

*Base.*—Attenuate to acute.

*Margin.*—Entire.

*Texture, upper and lower surfaces.*—Hirsute.

*Venation pattern.*—Pinnate; arcuate.

*Color.*—Developing foliage, upper surface: Close to 137C to 137D. Developing foliage, lower surface: Close to 137D. Fully expanded foliage, upper surface: Close to 137A to 137B; venation, close to 144A. Fully expanded foliage, lower surface: Close to 139D; venation, close to 145A.

*Petioles.*—Length:. About 2 mm to 4 mm. Diameter: About 1 mm. Texture, upper and lower surfaces: Hirsute; more on lower surface. Color, upper and lower surfaces: Close to 145A.

Flower description:

*Flower arrangement and habit.*—Single salverform flowers arranged singly arising from upper leaf axils. Freely flowering habit with usually about 150 flowers developing per plant.

*Flowers not persistent.*—Flowers face upwards and outwardly.

*Fragrance.*—None detected.

*Natural flowering season.*—Plants of the new *Calibrachoa* initiate and develop flowers about eight to ten weeks after planting. Plants flower continuously during the summer in Hillscheid, Germany.

*Flower longevity.*—Individual flowers last about five to eight days on the plant.

*Flower diameter.*—About 2.7 cm to 3 cm.

*Flower length* (*height*); About 2.5 cm to 2.7 cm.

*Corolla tube length.*—About 1.5 cm to 1.7 cm.

*Flower bud.*—Shape: Oblong to tubular. Length: About 2.3 cm to 2.5 cm. Diameter: About 4 mm to 7 mm. Color: Close to 1A to 1C; towards the apex, between 31D and 37B; fine lines, close to N186A.

*Corolla.*—Arrangement: Five petals fused at the base and opening into a flared trumpet; flowers star-shaped. Petal shape: Roughly obovate. Petal apex: Weakly rounded or truncate. Petal margin: Entire; weakly undulate. Petal texture, upper surface: Papillose, glabrous; satiny. Petal texture, lower surface: Hirsute along veins. Color: Petal, when opening, upper surface: Close to either 29A or 37B; towards the margins, close to 51B; towards the throat, close to 46B. Petal, when opening, lower surface: Close to either 24C or 38B. Petal, fully opened, upper surface: Close to 33D; towards the throat, close to 45A; venation, close to between 37A and 38C. With development, color becoming closer to either 29C or 36A; towards the throat, close to 43A. Petal, fully opened, lower surface: Close to either 37D or 38D. Throat: Close to 20A. Tube: Close to between 11A and 162B.

*Calyx.*—Arrangement: One star-shaped calyx tube with five sepals fused at the base per flower. Sepal length: About 1.5 cm to 1.6 cm. Sepal width: About 2.5 mm to 4 mm. Sepal shape: Narrowly lanceolate. Sepal apex: Obtuse to rounded. Sepal margin: Entire. Sepal texture, upper and lower surfaces: Densely hirsute. Color, upper and lower surfaces: Close to 137A.

*Peduncles.*—Length: About 1.3 cm to 1.8 cm. Diameter: About 1 mm. Strength: Moderately strong; flexible. Texture: Hirsute. Color: Close to 144C.

*Reproductive organs.*—Stamens: Quantity/arrangement: About five per flower. Filament length: About 9 mm to 12 mm. Filament diameter: Less than 1 mm. Filament color: Close to 150D. Anther shape: Reniform, two-parted. Pollen amount: Moderate. Pollen color: Close to 8B. Pistils: Quantity: One per flower. Pistil length: About 9 mm. Style color: Close to 145D. Stigma shape: Ovate. Stigma color: Close to 145B. Ovary color: Close to 145D.

*Seeds/fruits.*—Seed and fruit development have not been observed.

Garden performance: Plants of the new *Calibrachoa* have been observed to have good garden performance and tolerate wind, rain and temperatures ranging from about 5° C. about 30° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Cal Peachy' as illustrated and described.

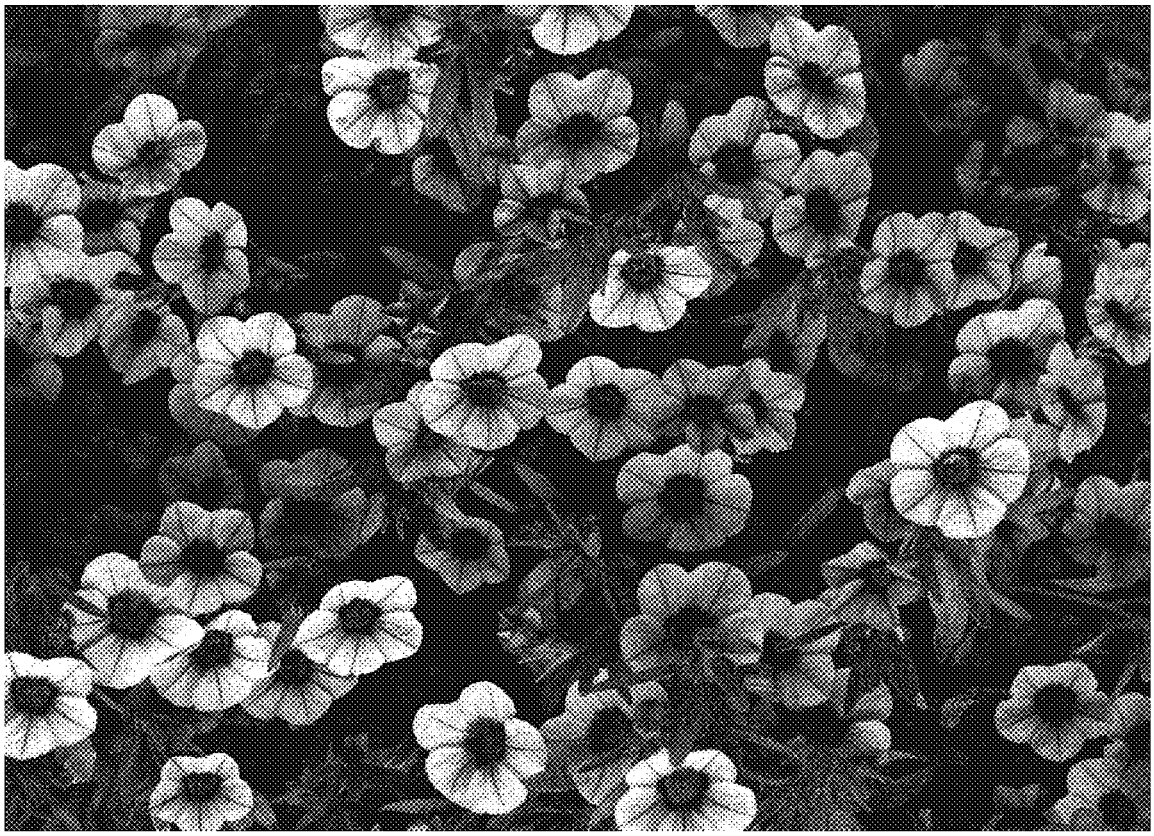

* * * * *